(12) United States Patent
Stewart et al.

(10) Patent No.: US 11,529,447 B2
(45) Date of Patent: Dec. 20, 2022

(54) METHOD FOR PERITONEAL REMOVAL OF ELECTROLYTES AND INFLAMMATORY MEDIATORS

(71) Applicant: Government of the United States as Represented by the Secretary of the Air Force, Wright-Patterson AFB, OH (US)

(72) Inventors: Ian Stewart, Lodi, CA (US); Jonathan Sosnov, San Antonio, TX (US); James Ross, Portland, OR (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 350 days.

(21) Appl. No.: 16/857,782

(22) Filed: Apr. 24, 2020

(65) Prior Publication Data
US 2020/0254168 A1    Aug. 13, 2020

Related U.S. Application Data

(62) Division of application No. 15/783,094, filed on Nov. 13, 2017, now abandoned.

(60) Provisional application No. 62/410,136, filed on Oct. 19, 2016.

(51) Int. Cl.
*A61M 1/28* (2006.01)
*B01D 15/34* (2006.01)

(52) U.S. Cl.
CPC .............. *A61M 1/285* (2013.01); *A61M 1/28* (2013.01); *A61M 1/287* (2013.01); *B01D 15/34* (2013.01); *A61M 2202/0468* (2013.01); *A61M 2205/04* (2013.01); *A61M 2205/75* (2013.01)

(58) Field of Classification Search
CPC ........ A61M 1/28; A61M 1/285; A61M 1/287; A61M 2202/0468; A61M 2205/04; A61M 2205/75; B01D 15/34
See application file for complete search history.

(56) References Cited

U.S. PATENT DOCUMENTS

2004/0082903 A1* 4/2004 Micheli .................. A61M 1/28
604/29
2006/0058731 A1* 3/2006 Burnett ............... A61M 1/1668
604/29

* cited by examiner

*Primary Examiner* — Amber R Stiles
(74) *Attorney, Agent, or Firm* — AFMCLO/JAZ; Chastity D. S. Whitaker (57) ABSTRACT

A method of peritoneal removal of electrolytes and inflammatory mediators. The method begins with infusing a treatment solution into the peritoneal cavity of a patient by way of a catheter. The treatment solution is drained from the peritoneal cavity by way of the catheter. During the draining, the treatment solution is filtered for removing electrolytes and inflammatory mediators.

5 Claims, 11 Drawing Sheets

METHOD FOR PERITONEAL REMOVAL OF ELECTROLYTES AND INFLAMMATORY MEDIATORS

This application is a divisional of U.S. application Ser. No. 15/783,094 filed on Oct. 13, 2017, which claimed the benefit of and priority to prior filed Provisional Application Ser. No. 62/410,135, filed Oct. 19, 2016. Each of these applications is expressly incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to peritoneal dialysis and, more particularly, to methods of binding electrolytes or inflammatory mediators.

BACKGROUND OF THE INVENTION

While severe illness or injury is, in itself, difficult for the patient and physician treatment, these conditions are often further complicated by increased levels of electrolytes and inflammatory mediators. Conventionally, electrolyte removal involves renal replacement therapy, which requires significant supplies and personnel. Such demands on resources makes in-field treatment at least difficult if not impossible. Likewise, inflammatory mediators are conventionally removed via continuous venovenous hemodialysis, plasma exchange, or hemoperfusion. Again, there is a significant requirement of resources, thus limiting it use during deployment.

Figure 1:
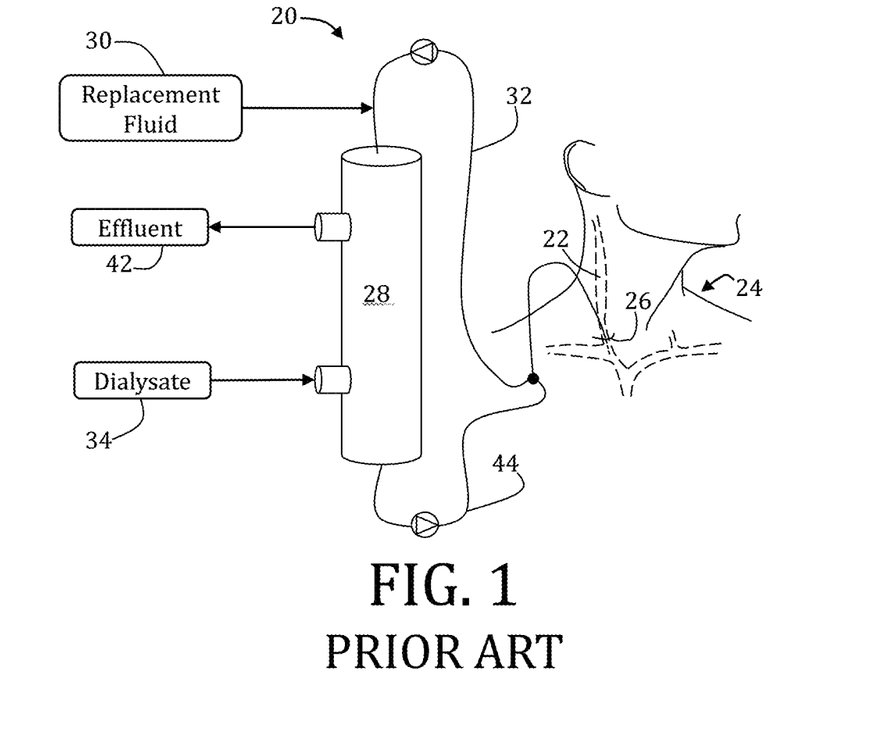
FIG. 1 is a schematic illustration of a renal replacement therapy treatment system according to the prior art.
Figure 1A:
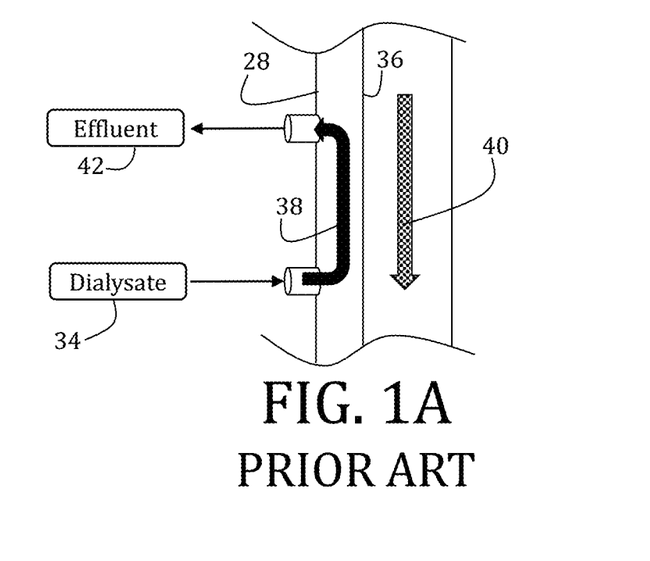
FIG. 1A is an enlarged portion of FIG. 1.

In either instance, treatment requires large bore catheterization to a major vein. For example, FIG. 1 illustrates one conventional renal replacement therapy treatment system 20 in which a venous access is made by way of a jugular vein 22 of a patient 24. A large bore catheter 26 extends from the jugular 22 and is fluidically coupled to an externally positioned blood filter 28. Oftentimes, a replacement fluid 30 may be introduced to the line 32 before the filter 28 (as illustrated), after the filter (not shown), or both. The replacement fluid 30 may comprise electrolytes and other chemical agents prone to removal during dialysis. A dialysate 34 is supplied to the filter 28, but such that the dialysate 34 is fluidically separated from the blood (such as by a semipermeable membrane 36 (FIG. 1A)) and in a direction of flow (arrow 38, FIG. 1A) that counters a direction of the blood flow (arrow 40, FIG. 1A). Thus, waste dialysate with other filtered waste products may be removed as part of an effluent 42. In any event, the dialysate 34 is configured to create a concentration gradient that draws small molecule wastes and electrolytes out of the blood flow (arrow 40), across the semipermeable membrane 36, and into the dialysate flow (arrow 38) at the effluent 42. Cleaned blood may then flow via another blood line 44 to the jugular 22.

While the exemplary system of FIG. 1 provides a significant benefit to patients, there remains need for improvements, particularly for use in the deployment field or for in-the-field use. For example, the illustrated treatment often creates complications in possible hemodynamic instability and typically requiring anticoagulation.

Given such difficulties in treating complications associated illness and injury, there remains a need for methods of peritoneal removing of electrolytes and inflammatory mediators that minimizes the need of resources and thus accessible for deployment and in-the-filed use.

SUMMARY OF THE INVENTION

The present invention overcomes the foregoing problems and other shortcomings, drawbacks, and challenges of conventional methods of removing peritoneal electrolytes and inflammatory mediators. While the invention will be described in connection with certain embodiments, it will be understood that the invention is not limited to these embodiments. To the contrary, this invention includes all alternatives, modifications, and equivalents as may be included within the spirit and scope of the present invention.

According to an embodiment of the present invention, a method of peritoneal removal of electrolytes and inflammatory mediators begins with infusing a treatment solution into the peritoneal cavity of a patient by way of a catheter. The treatment solution is drained from the peritoneal cavity by way of the catheter. During the draining, the treatment solution is filtered for removing electrolytes and inflammatory mediators.

In accordance with other embodiments of the present invention, the method includes elevating a treatment solution container above an infusion site of a patient such that the treatment solution infuses into the peritoneal cavity of the patient by way of a catheter. The treatment solution container may be lowered to below the infusion site so as to drain the treatment solution from the peritoneal cavity. Electrolytes and inflammatory mediators may be filtered from the treatment solution during infusion, during draining, or both.

Yet other embodiments of the present invention are directed to a method of peritoneal removal of electrolytes and inflammatory mediators and includes implanting a filter cartridge into the peritoneal cavity of a patient. The filter cartridge includes a binding agent enclosed within a porous surgical packing material. A treatment solution is infused into the peritoneal cavity of the patient and drawn from the peritoneal cavity by way of the filter cartridge.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 2:
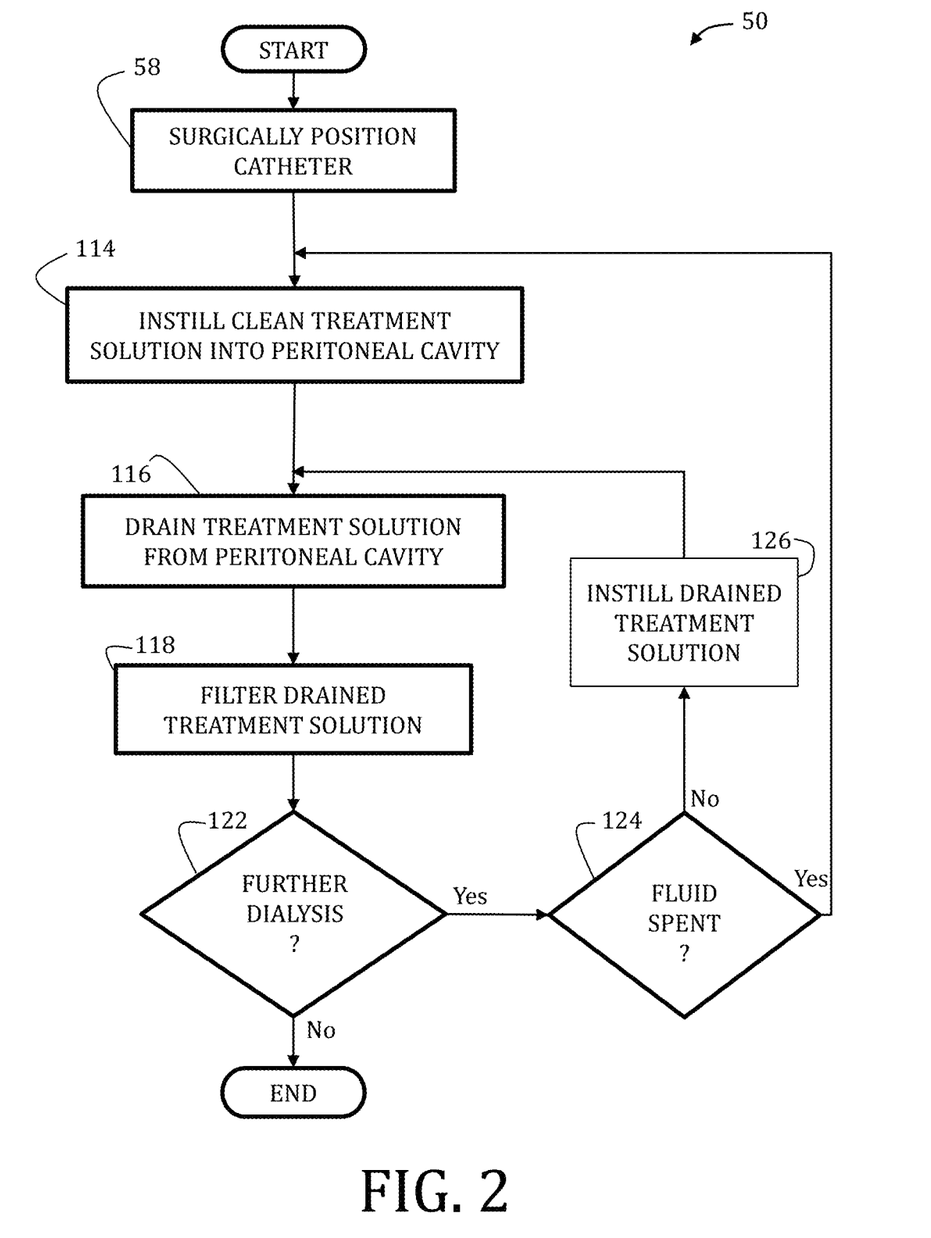
FIG. 2 is a flow chart illustrating a method of using a peritoneal dialysis system according to an embodiment of the present invention.
Figure 3:
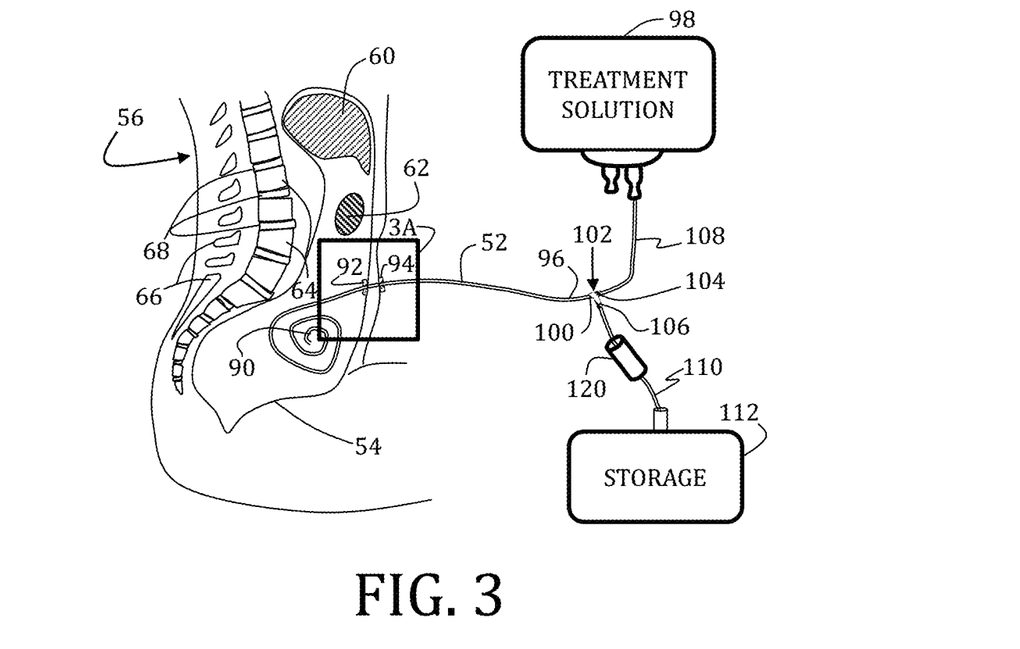
FIG. 3 is a schematic illustration of a peritoneal dialysis system according to an exemplary embodiment of the present invention.

Referring now to the figures, and in particular to FIGS. 2 and 3 (and reference to FIGS. 3A-6), a flowchart 50 illustrating a method of peritoneal dialysis configured to remove electrolytes and inflammatory agents according to a first embodiment of the present invention is described. At start, a peritoneal catheter 52 is surgically placed within the peritoneal cavity 54 of a patient 56 (Block 58). Insertion of the peritoneal catheter 52 may be accomplished via orthoscopic procedures, percutaneous procedures, or open surgical procedures. For purposes of illustration of a first embodiment of the present invention, a percutaneous procedure is illustrated. Additionally, to facilitate illustration, certain anatomical landmarks are also illustrated in FIG. 3, including the liver 60, stomach 62, vertebra bodies 64, spinous processes 66, and intervertebral discs 68.

Figure 4A:
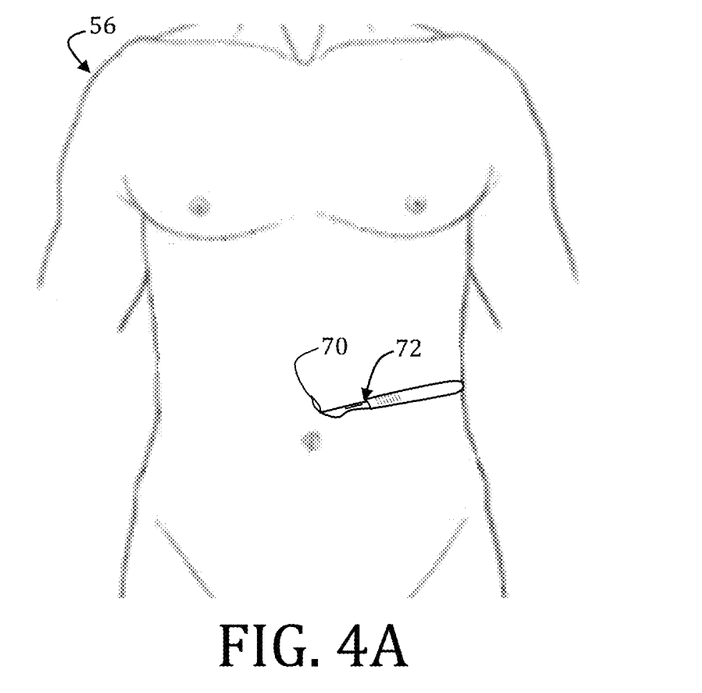
FIGS. 4A-4G are diagrammatic views illustrating successive steps of one exemplary procedure for implementing a peritoneal dialysis system.

Referring now to FIG. 4A, a small incision 70 is made using a blunt dissection tool, such as a scalpel 72. As is shown, the incision 70 may be along the midline, but the position of the incision 70 is not limiting and may be otherwise positioned if needed or desired by the surgeon. Further, it will be understood by those of ordinary skill in the art of percutaneous surgical procedures that the referenced illustrations are not necessarily to scale.

Figure 4B:
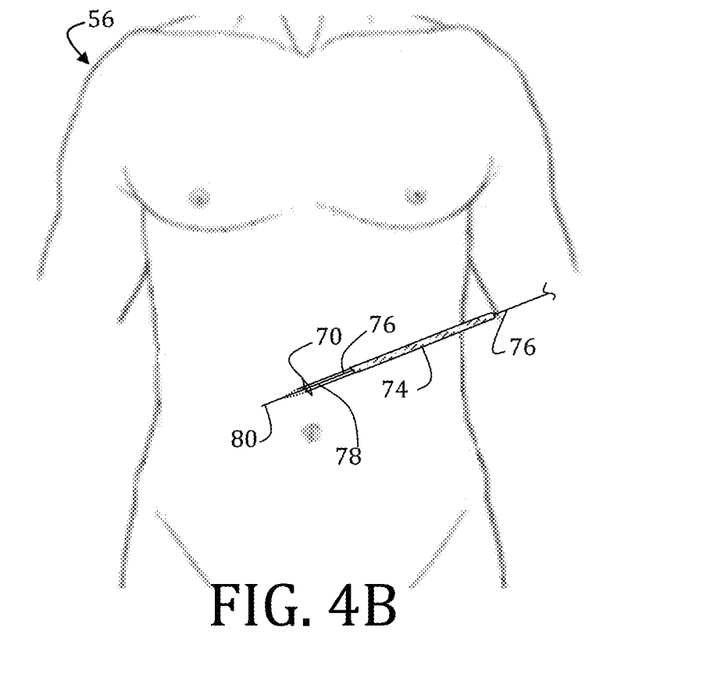

As illustrated in FIG. 4B, after the incision 70 is made, a needle 74 (illustrated in partial cross section) is inserted through the incision 70 and into the peritoneal cavity 54 (FIG. 3). While the specifics of the needle 74 are not necessary, for purposes of explanation, a suitable needle 74 may include an 18 gauge needle. To ensure appropriate positioning of the needle 74 and to increase maneuverability within the peritoneal cavity 54 (FIG. 3). Although not specifically illustrated here, air or saline may be injected into the peritoneal cavity 54 (FIG. 3) by way of the needle 74. While the volume of air or saline may vary and depends on a particular size of the patient's anatomy, 500 mL may be appropriate.

FIG. 4B further illustrates insertion of a guidewire 76 through a lumen (defined by an inner wall 78) of the needle 74 and into the inflated peritoneal cavity 54 (FIG. 3). With a distal end 80 of the guidewire 76 extending through the incision 70 and into the peritoneal cavity 54 (FIG. 3), the needle 74 may be retracted, over the length of the guidewire 76, and removed from a proximal end (not shown) of the guidewire 76. As such, the guidewire 46 remains positioned for receiving and guiding appropriate devices into the peritoneal cavity 54 (FIG. 3).

Figure 4C:
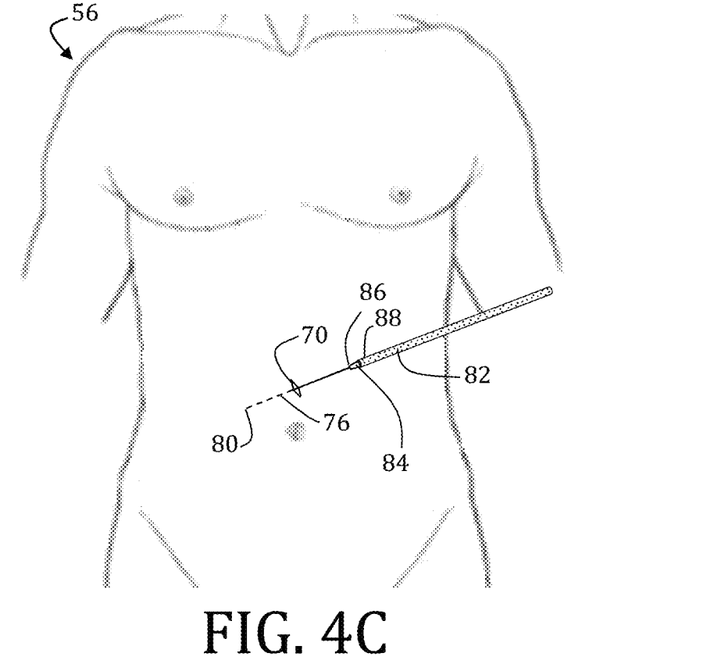
Figure 4D:
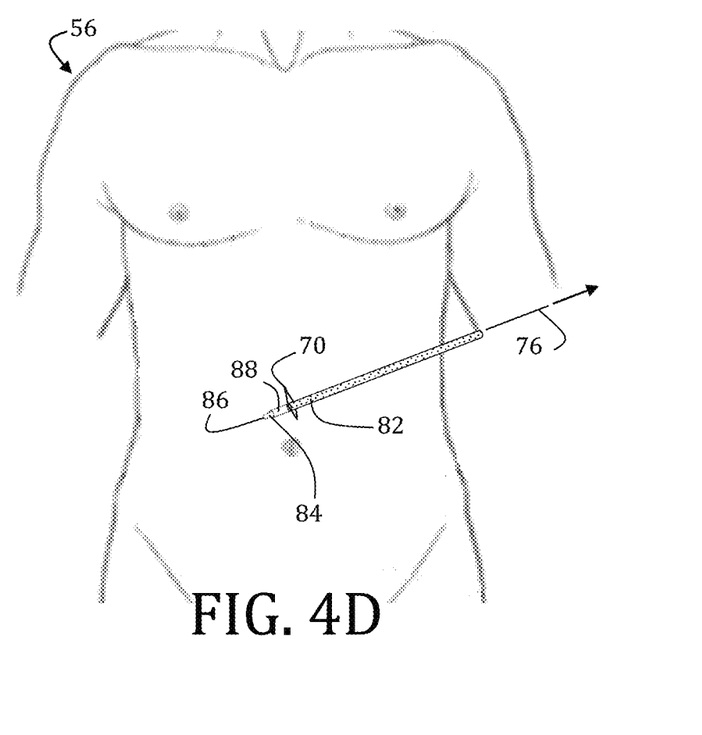
Figure 4E:
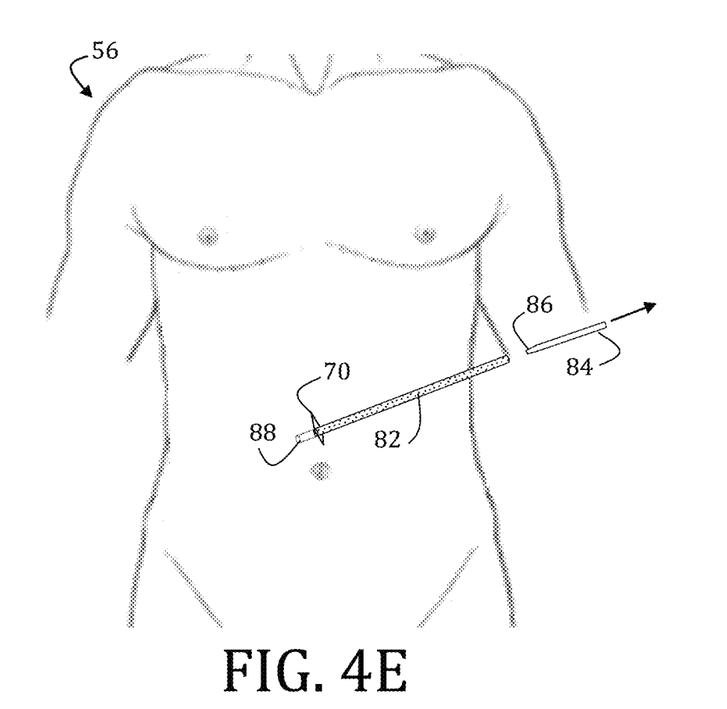

FIGS. 4C-4E illustrate insertion of a delivery sheath 82, optionally with a dilator 84, into the peritoneal cavity 54 (FIG. 3) by way of the guidewire 76. Specifically, in FIG. 4C, the optionally dilator 84 is positioned within a lumen (not shown) of the delivery sheath 82 such that a tapered distal end 86 of the dilator 84 extends distally away from a distal end 88 of the delivery sheath 82. Relative positioning of the dilator 84 and delivery sheath 82 may be secured in a manner that is known to the skilled surgeon. Suitable dilators 84 may include, but are not limited to, a rigid obturator, an inflatable dilating balloon, or other suitable dilator instrument.

The combination dilator 84 and delivery sheath 82 are directed, in unison, over the guidewire 76 toward the incision 70. As the dilator 84 and delivery sheath 82 move across the incision 70 and into the peritoneal cavity 54 (FIG. 3), the tapered end 86 of the dilator 84 dilates and expands the incision 70 such that the delivery sheath 82 may be received into the peritoneal cavity 54 (FIG. 3), which is shown in FIG. 4D.

As shown in FIG. 4E, once the delivery sheath 82 is in place, the dilator 86 may be retracted and removed while the distal end 88 of the delivery sheath 82 remains positioned within the peritoneal cavity 54 (FIG. 3).

Figure 4F:
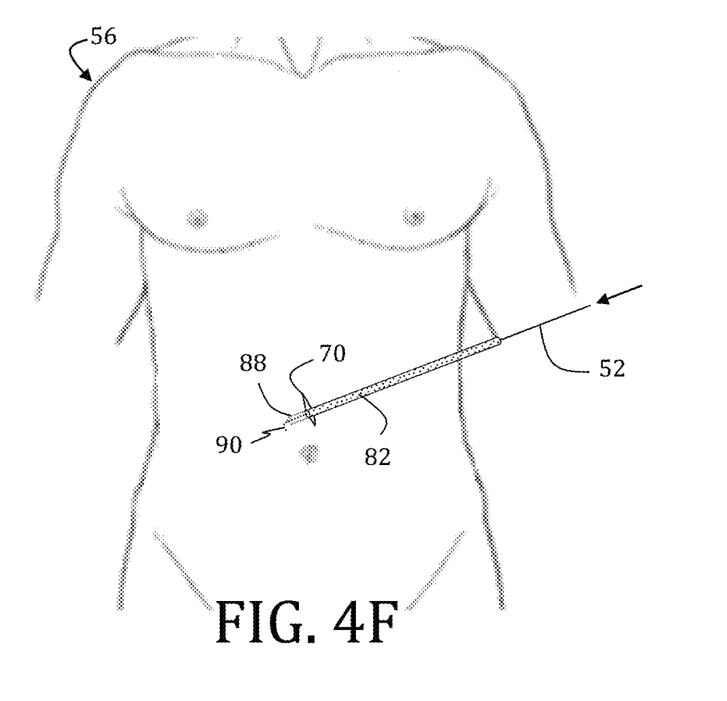
Figure 4G:
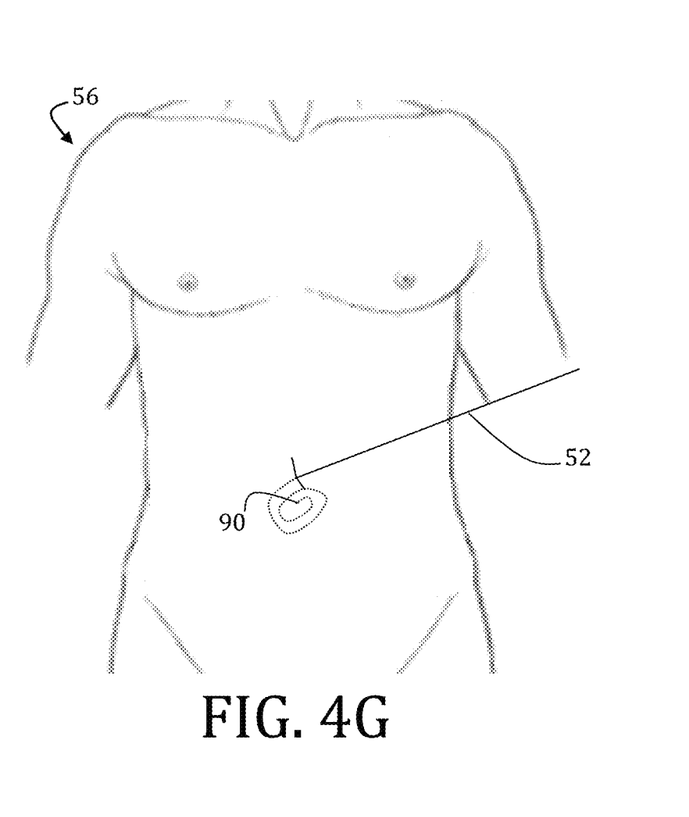

Looking now to FIG. 4F, the peritoneal catheter 52 may be advanced into the peritoneal cavity 54 (FIG. 3) by passing the catheter 52 through a lumen (not shown) of the delivery catheter 82. The particular peritoneal catheter 52 used may vary, but is generally selected from straight, swan neck, and coiled. If a coiled catheter is used, then, optionally, a removable stylet (not shown) may be positioned within a lumen of the coiled peritoneal catheter so as to resist coiling of the distal end of the catheter as the catheter emerges from the distal end 88 of the delivery sheath 82. Otherwise, the lumen (not shown) of the delivery sheath 82 may be sufficient to maintain the peritoneal catheter 52 in a relatively straight configuration until positioning within the peritoneal cavity 54 (FIG. 3) is complete. Thus, while FIGS. 4F and 4G illustrate use of a coiled peritoneal catheter 54, specific use of a stylet is not illustrated. Instead, as a distal end 90 of the peritoneal catheter 54 extends distally away from the distal end 88 of the delivery sheath 82, the distal end 90 of the catheter 52 may begin to coil. Further distally directed advancement of the catheter 52 through the delivery sheath 82 and into the peritoneal cavity 54 (FIG. 3) may permit further coiling of the distal end 90 of the peritoneal catheter 52, as shown in FIG. 3.

Figure 3A:
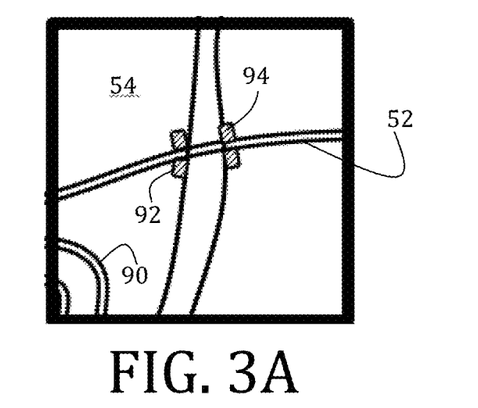
FIG. 3A is an enlargement of the portion identified in FIG. 3.

Referring again to FIG. 3, proper positioning of the peritoneal catheter 52 may be facilitated by way of one or more cuffs, which is more clearly shown in enlarged FIG. 3A. Specifically as illustrated, the peritoneal catheter 52 includes a first cuff 92 and a second cuff 94 positioned proximally to the first cuff 92. The first and second cuffs 92, 94 may be spaced along the peritoneal catheter 52 by a distance that is approximately equal to a thickness of the abdominal wall of the patient 56. In use, the surgeon may advance the peritoneal catheter 52 until the first cuff 92 is located within the peritoneal cavity 54. It would be understood that other catheters having only one cuff or no cuffs may also be used.

Turning now to FIG. 4G, and with the peritoneal catheter 52 suitably positioned within the peritoneal cavity 54 (FIG. 3), the delivery sheath 82 (FIG. 4F) may be removed. Removal may include retraction and withdrawal of the delivery sheath 82 (FIG. 4F) from the peritoneal cavity 54 (FIG. 3), the incision 70, and the catheter 52. Alternatively, the delivery sheath 82 (FIG. 4F) may comprise a peel-a-way material known by those of ordinary skill in the art. In that way, the delivery sheath 82 (FIG. 4F) may be split and peeled away from the catheter 52 and disposed.

Optionally, if necessary, the incision 70 may be closed to further secure placement of the catheter 52 within the peritoneal cavity 54 (FIG. 3).

Referring again to FIGS. 2 and 3, with the peritoneal catheter 52 positioned and secured, a proximal end 96 of the catheter 52 may be coupled a treatment solution source 98. Specifically as shown, the proximal end 96 of the catheter 52 is coupled to a first port 100 of a three-way valve 102. Two additional ports 104, 106 of the three-way valve 102 (second and third respectively) are further coupled to additional catheters 108, 110 of which one is operably coupled to the treatment solution source 98 and the other is operably coupled to a liquid storage tank 112.

Fluid flow through the three-way valve 102 may be configured such that treatment solution flows into and through the peritoneal catheter 52 and into the peritoneal cavity 54, permitting the treatment solution to be instilled into the cavity 54 (Block 114). The treatment solution comprises saline with optional binding agents. According to some embodiments of the present invention, the binding agents may be chelators configured to absorb inflammatory mediators, metals, or other solutes from the peritoneal cavity 54.

After a period of time, sufficient for achieving equilibration, the treatment solution may be drained from the peritoneal cavity 52, via the peritoneal catheter 52 and three-way valve 106 to the fluid storage tank 112 (Block 116). The treatment solution is filtered (Block 118), which may accomplished after being drained into the fluid storage tank 112 or, as specifically illustrated, as the treatment solution flows through the catheter 110 extending between the three-way valve 106 and the fluid storage tank 112. As such, the fluid path along the catheter 110 includes a filter 120 configured to remove inflammatory mediators.

According to some embodiments of the present invention, the filter 120 may incorporate a polymer, such as those described in U.S. Application Publication No. 2013/0195792, entitled METHOD OF TREATING INFLAMMATION, and filed on Apr. 1, 2011; U.S. Application Publication No. 2014/0294751, entitled HEMOCOMPATIBILITY MODIFIERS FOR CROSS-LINKED POLYMERIC MATERIAL, and filed Mar. 31, 2014; or U.S. Application Publication no. 2015/0118673, entitled POLYMERIC SORBENT FOR REMOVAL OF IMPURITIES FROM WHOLE BLOOD AND BLOOD PRODUCTS, and filed Aug. 10, 2012. Such polymer is configured to remove inflammatory mediators via the principle of size exclusion (molecules of the intended size are trapped within the polymer structure).

According to other embodiments of the present invention, binding agents may comprise resins, diffusion tubes, or other novel binding agents, including, for example, those that are described in U.S. Pat. No. 8,216,560, issued on Jul. 10, 2012, and entitled ION BINDING POLYMERS AND USES THEREOF.

Once the treatment solution has drained into the fluid storage tank 112, and filtered, a determination as to whether further dialysis is made (Decision Block 122). Such determination may include, for example, laboratory analysis of the blood, analysis of electrocardiogram, or clinical evaluation by a physician. If further dialysis is required ("YES" branch of decision block 122), then a further determination as to whether the treatment solution is spent is made (Decision Block 124). Said another way, if the drained and filtered treatment solution within the fluid storage tank 112 has inflammatory mediators above a threshold concentration ("YES" branch of decision block 124), then the process may return to instilling clean treatment solution into the peritoneal cavity (Block 114). However, if the concentration of inflammatory mediators within the drained and filtered treatment solution in the fluid storage tank 112 is below such threshold concentration ("NO" branch of decision block 124), then treatment solution within the fluid storage tank 112 may be instilled into the peritoneal cavity 52 (Block 126) and the process continues.

If further dialysis is neither required nor desired ("NO" branch of decision block 122), then the process ends.

Figure 5:
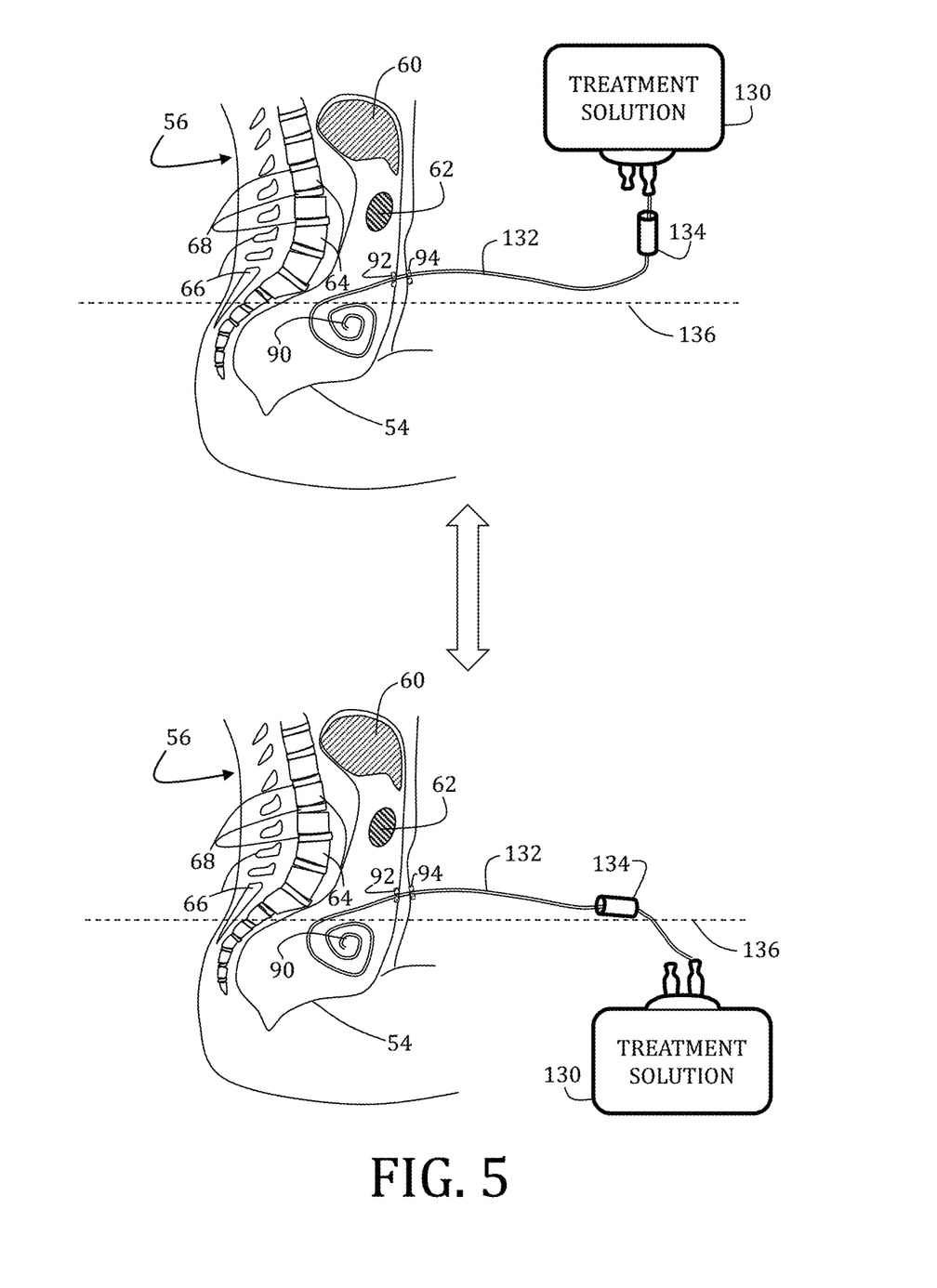
FIG. 5 is a diagrammatic illustration of a method of using a peritoneal dialysis system according to an embodiment of the present invention.

An alternative embodiment of the present invention is illustrated in FIG. 5. More particularly the peritoneal cavity 54 may be fluidically coupled to a treatment solution container 130 via a catheter 132 having a filter 134 along the fluid path. At start, the treatment solution container 130 may be elevated to above a level (illustrated by a dashed line 136) of the peritoneal cavity 54. The treatment solution thus flows down, by gravity, from the treatment solution container 130, through the filter 134, to the peritoneal cavity 54. After a time suitable for reaching equilibration, the treatment solution container 130 may be lowered to below the level (line 136) such that the treatment solution drains, by gravity, from the peritoneal cavity 54, through the filter 134 and to the treatment solution container 130. While the treatment solution drains and flows through the filter, electrolytes and inflammatory mediators, or both, are removed from solution, as described previously. Once these substances are filtered and bound, the treatment solution container 130 may then, again, be raised such that the treatment solution is re-instilled into the peritoneal cavity 54. The process may be repeated until the therapeutic effect has been achieved (e.g., resolution of hyperkalemia).

While not specifically illustrated, yet another embodiment is envisioned in which the filter may be incorporated into the treatment solution container 130 as opposed to being an inline filter.

Figure 6:
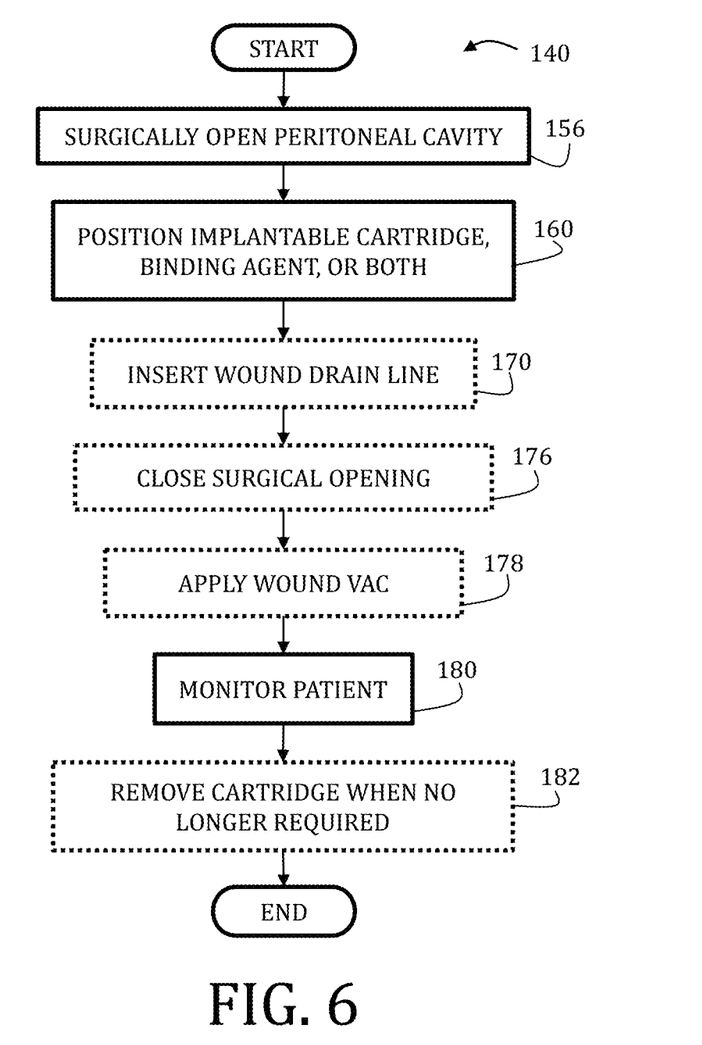
FIG. 6 is a flow chart illustrating a method of using a peritoneal dialysis system according to another embodiment of the present invention.
Figure 8:
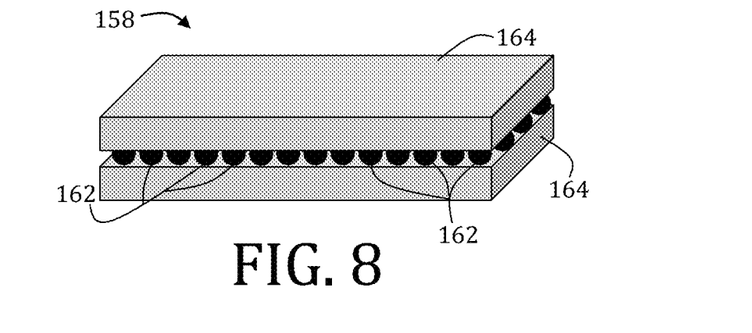
FIG. 8 is a schematic illustration of a peritoneal dialysis system according to another exemplary embodiment of the present invention.

With reference now to FIGS. 6-8, a method 140 of peritoneal dialysis according to other embodiments of the present invention is shown. While this particular illustrated embodiment incorporates an open surgical procedure, it would be understood that the method could be performed in other ways, such a laparoscopically. While not necessary, this particular embodiment of the present invention is likely to be used when the abdomen 142 of the patient 144 is opened during a planned trauma surgery. Nonetheless, as shown in FIG. 7A, an incision 146 may be created with a scalpel 147 in the subcutaneous layer dissected to and through the sheath of the rectus abdominal muscle. Thereafter, the peritoneum is dissected, the peritoneal cavity 148 opened and inspected for adhesions (FIG. 7B). FIG. 7B specifically illustrates the peritoneal cavity 148 with the liver 150, stomach 152, and intestines 154 exposed (Block 156).

Figure 7A:
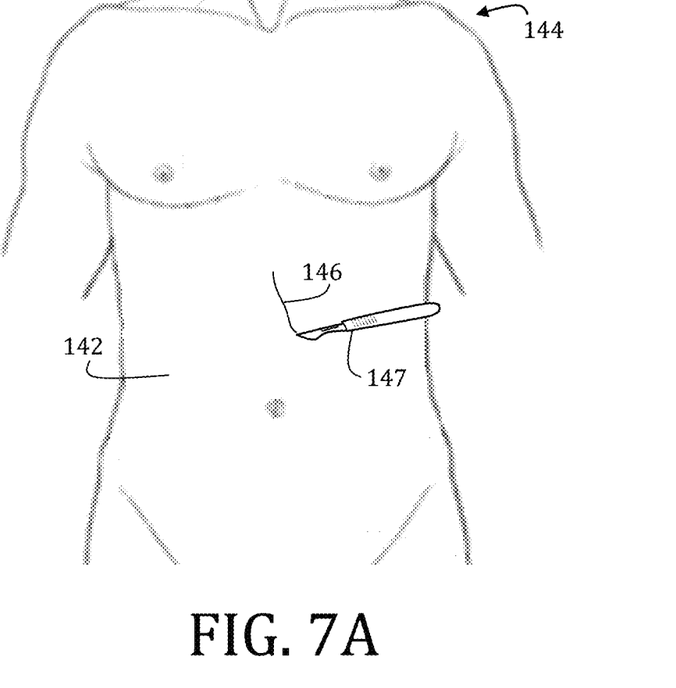
FIG. 7A-7D are diagrammatic views illustrating successive steps of one exemplary procedure for implanting the peritoneal dialysis system of FIG. 8.
Figure 7B:
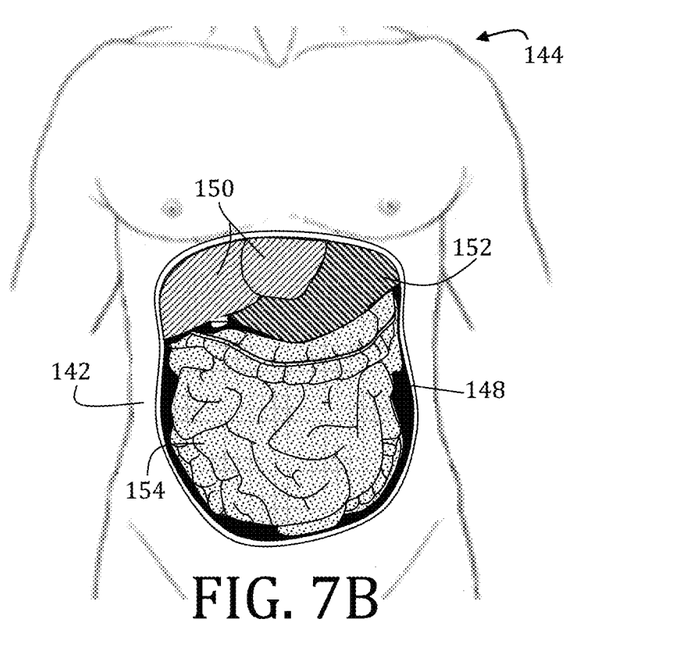
Figure 7C:
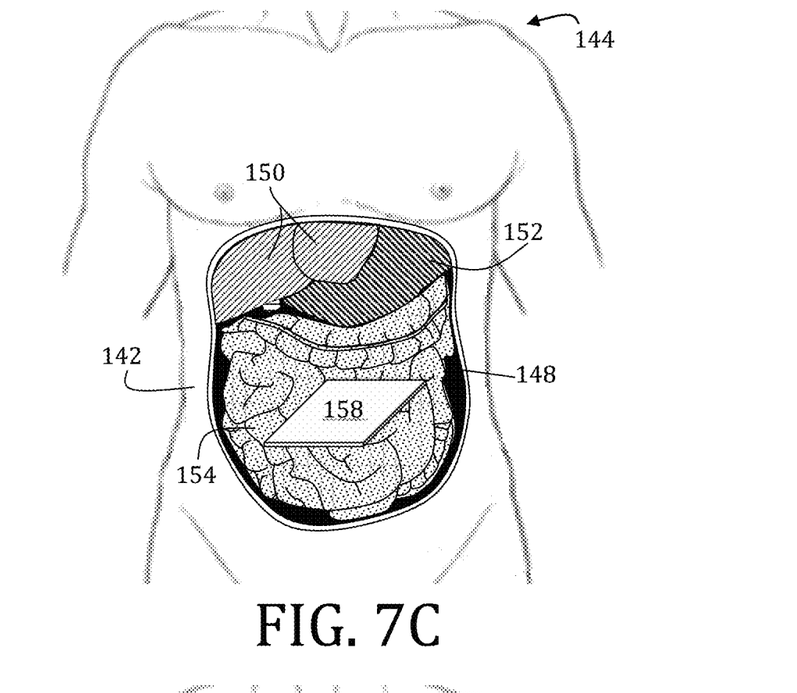

In FIG. 7C, an implantable cartridge 158, according to an embodiment of the present invention, may be placed within the peritoneal cavity 148 (Block 160). The implantable cartridge 158, which is illustrated with greater detail in FIG. 8, comprises binding agents 162, described previously, enclosed or others sandwiched between porous surgical packing materials 164, which may include gauze, laparotomy pads, or sponges.

While the implantable cartridge 158 is within the peritoneal cavity 148, electrolytes and inflammatory mediators, for example, potassium, may flow down a concentration gradient into that fluid. In the setting of hyperkalemia, the concentration of potassium can be 6 meq/L. With standard peritoneal dialysis, if 2 L of fluid (with a concentration of 0 meq/L of potassium) are infused into the peritoneum, potassium will flow down a concentration gradient until the concentrations equalize and a total of 12 meq (6 meq/L×2 L) will be removed. However once the concentrations equilibrate, no further substances transmit from the blood. The same process occurs for other electrolytes and inflammatory mediators. However, with the implantable cartridge 158 in the peritoneal cavity 148, the potassium would be bound, keeping the potassium concentration in the fluid at close to 0 meq/L, which would enable continued removal without exchange of fluid.

The position of the cartridge 158 may be largely dependent on surgeon preference, but should generally be in a location have sufficient surface area. To increase surface area available for binding, fluid may be instilled into the peritoneal cavity 148.

Figure 7D:
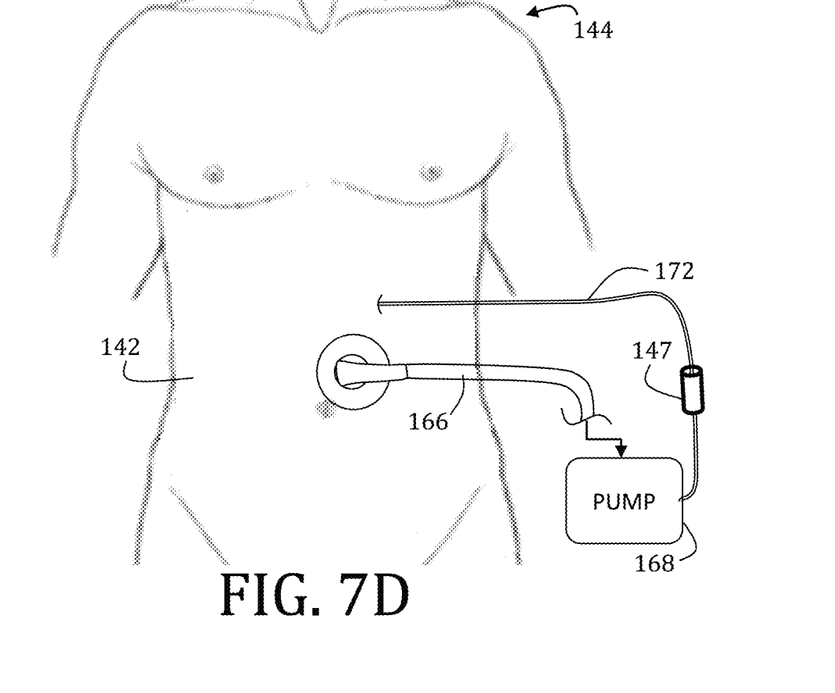

Turning now to FIG. 7D, with continued reference to FIGS. 6 and 8, a wound drain 166 and pump 168 may optionally applied to the surgical site in close proximity to the cartridge 158 (FIG. 7C) (Block 170). Further optionally, as illustrated, a fluid port of the pump 168 may be fluidically coupled to another catheter 172 that may lead to the peritoneal cavity 148. A filter 174, in accordance with those described in greater detail above, may be in fluid communication with and along the fluid path of the catheter 172.

If desired, the surgical opening may then be closed (Block 176). With the pump activated, a wound vacuum is applied (Block 178). In such arrangement, fluid extracted from the peritoneal cavity 148 by way of the wound drain 166 and pump 158 may be filtered and re-instilled to into the peritoneal cavity 158.

The patient 144 may be monitored (Block 180) until such a time that the cartridge 158, drain 166, pump 168, and filter 174 are no longer required and, thus, removed (Block 182).

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method of peritoneal removal of electrolytes and inflammatory mediators, the method comprising:
   implanting a filter cartridge in the peritoneal cavity of a patient;
   infusing a treatment solution into the peritoneal cavity of a patient; and
   drawing the treatment solution from the peritoneal cavity through the filter cartridge and pulling the treatment solution from the peritoneal cavity by way of a wound drain;
   wherein the filter cartridge comprises a binding agent enclosed within a porous surgical packing material.

2. The method of claim 1, wherein the wound drain is fluidically coupled to a pump.

3. The method of claim 1, further comprising:
   re-instilling the treatment solution into the peritoneal cavity.

4. The method of claim 1, wherein the binding agent is configured to selectively bind electrolytes, inflammatory mediators, or both.

5. The method of claim 4, wherein the binding agent is selected from the group consisting of:
   a polymer, a resin, or diffusion tubes configured to remove inflammatory mediators.

* * * * *